United States Patent
Foo et al.

(10) Patent No.: US 9,254,111 B2
(45) Date of Patent: Feb. 9, 2016

(54) PET ACQUISITION SCHEDULING BASED ON MR SCOUT IMAGES

(71) Applicant: General Electric Company, Schenectady, NY (US)

(72) Inventors: Thomas Kwok-Fah Foo, Clifton Park, NY (US); Christopher Judson Hardy, Niskayuna, NY (US); Charles William Stearns, Milwaukee, WI (US); Ravindra Mohan Manjeshwar, Glenville, NY (US); Florian Wiesinger, Garching (DE); Dattesh Dayanand Shanbhag, Bangalore (IN)

(73) Assignee: General Electric Company, Niskayuna, NY (US)

( * ) Notice: Subject to any disclaimer, the term of this patent is extended or adjusted under 35 U.S.C. 154(b) by 128 days.

(21) Appl. No.: 13/686,226

(22) Filed: Nov. 27, 2012

(65) Prior Publication Data
US 2014/0148684 A1 May 29, 2014

(51) Int. Cl.
*A61B 6/00* (2006.01)
*A61B 5/00* (2006.01)
*A61B 5/055* (2006.01)
(Continued)

(52) U.S. Cl.
CPC ............ *A61B 6/5247* (2013.01); *A61B 5/0035* (2013.01); *A61B 5/055* (2013.01); *A61B 5/7292* (2013.01); *A61B 6/02* (2013.01); *A61B 6/037* (2013.01); *A61B 6/04* (2013.01); *A61B 6/0407* (2013.01); *A61B 6/4417* (2013.01); *A61B 6/469* (2013.01); *A61B 6/488* (2013.01); *A61B 6/541* (2013.01); *A61B 6/542* (2013.01); *A61B 6/545* (2013.01); *A61B 5/0037* (2013.01);
(Continued)

(58) Field of Classification Search
CPC ........ A61B 6/5247; A61B 6/02; A61B 6/488; A61B 6/541; A61B 6/542; A61B 5/0035; A61B 5/055; A61B 5/0555
See application file for complete search history.

(56) References Cited

U.S. PATENT DOCUMENTS 6,700,373 B2   3/2004   Mueller et al.
7,652,259 B2   1/2010   Kimchy et al.
(Continued)

FOREIGN PATENT DOCUMENTS

DE   102008022816 A1   11/2009
WO      2008115593 A1    9/2008
(Continued)

OTHER PUBLICATIONS

Catana et al., Nonrigid PET motion compensation in the lower abdomen using simultaneous tagged-MRI and PET imaging, Medical Physics, vol. 38, No. 6, Jun. 2011.*
Aldefeld et al., "Continuously Moving Table 3D MRI with Lateral Frequency-Encoding Direction", Magnetic Resonance in Medicine, vol. 55, pp. 1210-1216, 2006.
Beyer et al., "MR-Based Attenuation Correction for Torso-PET/MR Imaging: Pitfalls in Mapping MR to CT data", European Journal of Nuclear Medicine and Molecular Imaging, vol. 35, pp. 1142-1146, Feb. 19, 2008.
(Continued)

*Primary Examiner* — Bo J Peng
(74) *Attorney, Agent, or Firm* — Robert M. McCarthy (57) ABSTRACT

Exemplary embodiments of the present disclosure are directed to scheduling positron emission tomography (PET) scans for a combined PET-MRI scanner based on an acquisition of MR scout images of a subject. An anatomy and orientation of the subject can be determined based on the MR scout images and the schedule for acquiring PET scans of the subject can be determined from the anatomy of the subject. The schedule generated using exemplary embodiments of the present disclosure can specify a sequence of bed positions, scan durations at each bed position, and whether respiratory gating will be used at one or more of the bed positions.

12 Claims, 5 Drawing Sheets

(51) Int. Cl.
*A61B 6/02* (2006.01)
*A61B 6/04* (2006.01)
*A61B 6/03* (2006.01)

(52) U.S. Cl.
CPC .......... *A61B 5/0555* (2013.01); *A61B 5/7289* (2013.01); *A61B 6/461* (2013.01); *A61B 6/548* (2013.01)

(56) References Cited

U.S. PATENT DOCUMENTS

| | | | |
|---|---|---|---|
| 7,835,782 B2 | 11/2010 | Cherry et al. | |
| 7,847,552 B2 | 12/2010 | Haworth et al. | |
| 7,888,632 B2 | 2/2011 | Ladebeck et al. | |
| 7,923,691 B2 | 4/2011 | Ladebeck | |
| 8,064,981 B2 | 11/2011 | Eberler et al. | |
| 8,089,279 B2 | 1/2012 | Martin et al. | |
| 2009/0182219 A1* | 7/2009 | Gericke et al. | 600/407 |
| 2010/0220909 A1 | 9/2010 | Thielemans et al. | |
| 2010/0290683 A1 | 11/2010 | Demeester et al. | |
| 2010/0329531 A1 | 12/2010 | Martinez-Moller et al. | |
| 2011/0123083 A1* | 5/2011 | Ojha et al. | 382/131 |
| 2011/0187364 A1 | 8/2011 | Blumhagen et al. | |

FOREIGN PATENT DOCUMENTS

| | | |
|---|---|---|
| WO | 2010094655 A1 | 8/2010 |
| WO | 2010097714 A2 | 9/2010 |

OTHER PUBLICATIONS

Hofmann et al., "MRI-Based Attenuation Correction for PET/MRI: A Novel Approach Combining Pattern Recognition and Atlas Registration", Journal of Nuclear Medicine, vol. 49, pp. 1875-1883, 2008.

Hofmann et al., "MRI-Based Attenuation Correction for Whole-Body PET/MRI: Quantitative Evaluation of Segmentation- and Atlas-Based Methods", The Journal of Nuclear Medicine, vol. 52, pp. 1392-1399, Sep. 2011.

Judenhofer et al., "Simultaneous PET-MRI: A New Approach for Functional and Morphological Imaging", Nature Medicine, vol. 14, pp. 459-465, published online Mar. 23, 2008.

Koken et al., "Towards Automatic Patient Position and Scan Planning Using Continuously Moving Table MR Imaging", Magnetic Resonance in Medicine; vol. 62, pp. 1067-1072, 2009.

Kops et al., "Alternative Methods for Attenuation Correction for PET Images in MR-PET Scanners", Nuclear Science Symposium Conference Record, 2007. pp. NSS '07. IEEE, 4327-4330, vol. 6, Jan. 22, 2008.

Kruger et al., "Continuously Moving Table Data Acquisition Method for Long FOV Contrast-Enhanced MRA and Whole-Body MRI", Magnetic Resonance in Medicine, vol. 47, pp. 224-231, 2002.

Zhu et al., "Extended Field-of-View Imaging With Table Translation and Frequency Sweeping", Magnetic Resonance in Medicine, vol. 49, pp. 1106-1112, 2003.

* cited by examiner

PET ACQUISITION SCHEDULING BASED ON MR SCOUT IMAGES

BACKGROUND

Positron Emission Tomography (PET) imaging involves the creation of tomographic images of positron emitting radionuclides in a subject of interest. Conventionally, a subject (e.g., a human patient) receives a PET agent, e.g., a radiopharmaceutical, and then is positioned within a PET imaging system that includes a detector and detection electronics. As the PET agent decays, positively charged anti-electrons (positrons) are emitted. For commonly used PET agents the positrons travel a few millimeters through the tissues of the subject before colliding with an electron, resulting in mutual annihilation. The positron/electron annihilation results in a pair of oppositely-directed gamma rays with approximately 511 keV energy.

When the gamma rays impinge on the detector, the detector emits light, which is detected by detection electronics. The signals corresponding to the emitted light are processed as incidences of gamma rays. When two gamma rays strike oppositely positioned scintillators of the detector at approximately the same time, a coincidence is registered. The coincidences are processed to identify true coincidence events, which are binned and integrated to form frames of PET data that can be reconstructed as images depicting the distribution of the PET agent in the subject.

Another technique employed in medical imaging is Magnetic Resonance Imaging (MRI), which conventionally uses a powerful magnet to create a strong, uniform, static magnetic field (i.e., the "main magnetic field") to polarize hydrogen nuclei in a subject's tissue so that the magnetic moments generally align along the direction of the main magnetic field. MRI systems conventionally include gradient coils that produce smaller amplitude (i.e. compared to the main magnetic field), spatially varying magnetic fields in response to an electric current control signal. Typically, gradient coils are designed to produce a magnetic field component that is generally aligned along the axis of the main magnetic field and that varies in amplitude with position along one or more axes. The effect of a gradient coil is to create a small ramp on the magnetic field strength and concomitantly on the resonant frequency of the nuclear spins, along a single axis. Three gradient coils with orthogonal axes are typically used to "spatially encode" the magnetic resonance (MR) signal by creating a signature resonance frequency at each location in the body. Radio frequency (RF) coils are used to create pulses of RF energy at or near the resonance frequency of the hydrogen nuclei. These coils are used to add energy to the nuclear spin system in a controlled fashion. As the nuclear spins then relax back to their rest energy state, they give up energy in the form of an RF signal, which can be detected by the MRI system as MR data, and combined with multiple additional such signals may be used to reconstruct an MR image using a computer and known algorithms.

In recent years, hybrid or combined PET-MRI scanners have been developed so that PET and MRI images can be acquired using a single medical imaging scanner. While these conventional combined PET-MRI scanners can offer efficiencies over separate and individual PET scanners and MRI scanners, the combination of the PET and MRI scanners into a single scanner presents difficult challenges in realizing such efficiencies and ensuring high quality image acquisition.

SUMMARY

Exemplary embodiments of the present disclosure are directed to generating PET scan schedules based on a series of MR scout images acquired for the subject. The acquired MR scout images can be used by exemplary embodiment of the present disclosure to determine an anatomy of the subject, which can be represented as an anatomy map. The schedule can be generated to account for the subject's anatomy to plan a sequence of PET scans that are specific to the subject. The schedule can be generated to specify a sequence of bed positions, scan durations/acquisition times, and whether respiratory gating will be used at the bed positions.

Exemplary embodiments of the present disclosure advantageously tailor PET scans based on a programmatically generated schedule based on an anatomy of a subject so that a combined PET-MRI scanner can step through bed positions specified in the schedule according to a specific patient's anatomy, taking into account factors such as whether the anatomy in the region of interest (e.g. lungs/diaphragm) is moving, and the anatomy's overall expected attenuation. Using exemplary embodiments of the present disclosure can advantageously allow for specifying bed position parameters such as bed position, acquisition time, and presence/absence of retrospective respiratory gating based for each patient to provide a custom PET scan schedule for each patient. The MR scout images can be advantageously acquired while the bed is advanced to an initial PET scan position in the PET-MRI scanner so that no additional time is required to plan for the PET scans to be acquired.

In one embodiment, a combined positron emission tomography (PET) and magnetic resonance imaging (MRI) system is disclosed that includes PET detector/imaging components, MRI components, and a processing device. The PET detector/imaging components form a PET scanner portion of the combined PET-MRI scanner and the MRI components form an MRI scanner portion of the combined PET-MRI scanner. The PET detector/imaging components constitute the PET scanner portion while the MRI components constitute the MRI scanner portion of the combined PET-MR scanner. The processing device is in communication with the MRI components to acquire a sequence of MR scout images of a subject via the MRI scanner portion and with the PET components to acquire a sequence of PET scans of the subject via the PET scanner portion and according to a schedule programmatically generated based on an anatomy of the subject determined from the MR scout images.

In another embodiment, a method of scheduling positron emission tomography (PET) scans with a combined PET-MRI scanner is disclosed. The method includes acquiring a sequence of MR scout images of a subject, determining an anatomy and an orientation of the subject based on the MR scout images, and generating a schedule for acquiring PET scans of the subject based on the anatomy of the subject determined from the MR scout images.

In yet another embodiment, a non-transitory computer-readable storage medium storing executable instructions is disclosed. Execution of the instructions by a processing device causes the processing device to implement a method that includes acquiring a sequence of MR scout images of a subject, determining an anatomy and an orientation of the subject based on the MR scout images, and generating a schedule for acquiring PET scans of the subject based on the anatomy of the subject determined from the MR scout images.

In some embodiments, a bed of the combined PET-MRI scanner can be moved along a longitudinal axis with respect to an MRI scanner portion of the combined PET-MRI scanner to acquire the sequence of MR scout images along at least a portion of a length of the bed.

In some embodiments, the schedule can include a sequence of bed positions with respect to a field of view of the PET scanner portion and can include an acquisition time associated with each of the bed positions. The PET scans of the sequence of PET scans can be acquired at each of the bed positions according to the acquisition time associated with the bed positions. The acquisition time is based on the anatomy of the subject determined from the MR scout images. The MR scout images are represented in an anatomy map and an orientation of the subject is determined based on the anatomy map.

In some embodiments, the individual PET scans of a sequence of overall PET scans for which respiratory gating is scheduled can be identified and/or the bed positions can be specified to separate moving anatomy PET scans from non-moving anatomy scans based on the MR scout images. As an example, the MR scout images identifies the region of the anatomy where a PET scan is scheduled. The anatomy that is identified determines the PET acquisition protocol that should be performed. If the anatomy is in the abdominal area where respiratory gating is required, the system automatically recognizes such a case and enables respiratory gating/motion compensation for the PET acquisition. If the anatomy is such that there is no motion compensation (for example in the pelvis or lower extremities) then respiratory gating is not required and is not scheduled for that specific PET acquisition.

In some embodiments, the bed can be moved along a longitudinal axis with respect to an MRI scanner portion of the combined PET-MRI scanner to acquire the MR scout images and the bed can be moved along the longitudinal axis with respect to the PET scanner portion of the combined PET-MRI scanner to acquire at least one of the PET scans of the sequence of PET scans at sequence of bed position according to the schedule.

Any combination or permutation of embodiments is envisioned. Other objects and features will become apparent from the following detailed description considered in conjunction with the accompanying drawings. It is to be understood, however, that the drawings are designed as an illustration only and not as a definition of the limits of the invention.

DESCRIPTION OF EXEMPLARY EMBODIMENTS

Exemplary embodiments of the present disclosure are directed to generating a schedule for PET data acquisition in a combined PET-MRI scanner based on acquired MR scout images. The acquired MR scout images can be used by exemplary embodiment of the present disclosure to determine an anatomy of the subject, which can be represented as an anatomy map. The schedule can be generated to account for the subject's anatomy to provide plan a sequence of PET scans that are specific to the subject. The schedule can be generated to specify a sequence of bed positions, scan durations/acquisition times, and whether respiratory gating will be used at the bed positions. The bed positions in the schedule can be specified to segment the scans into moving and non-moving anatomy based on the anatomy of the subject and the bed positions can be specified based on a height of the subject determined from the MR scout images.

Figure 1:
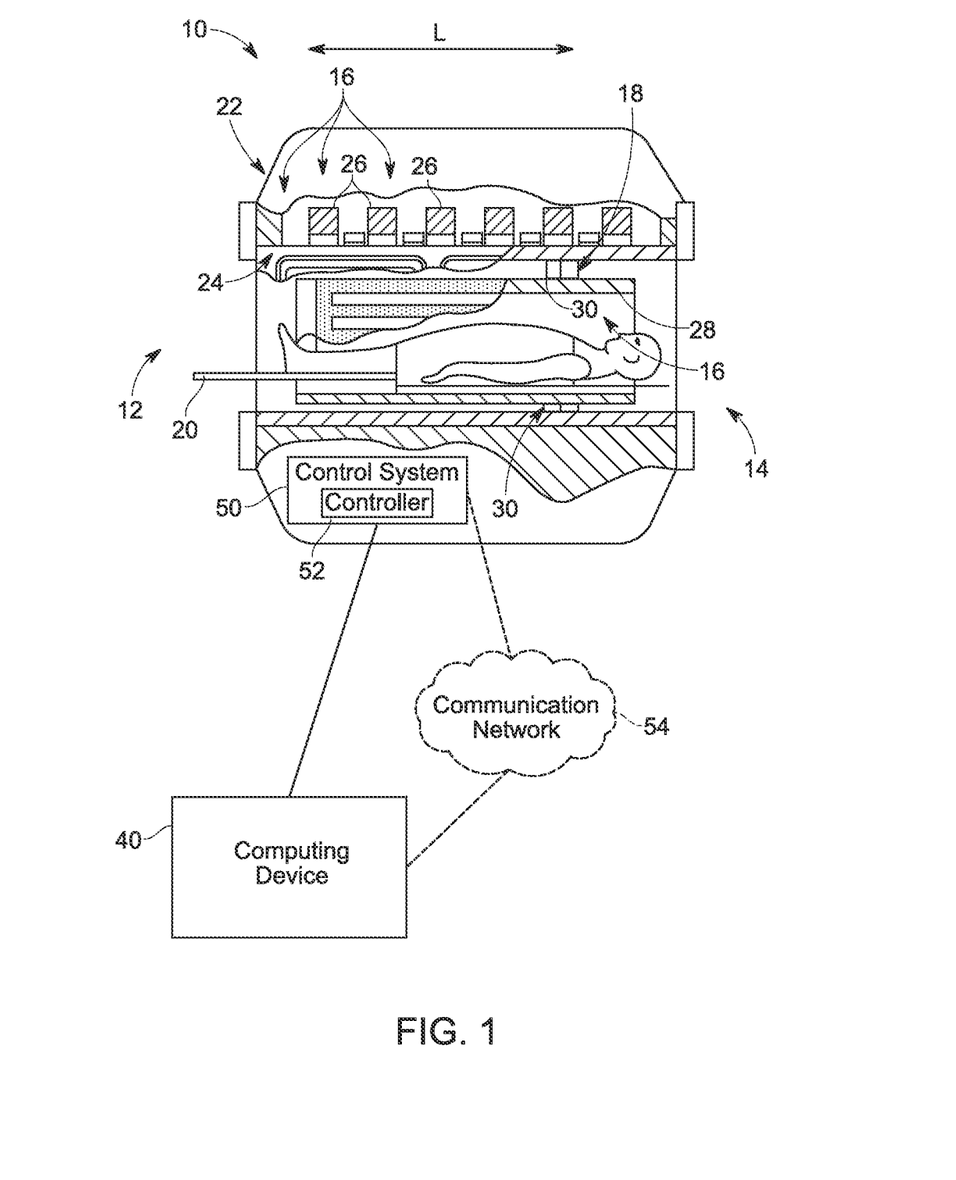
FIG. 1 illustrates an exemplary combined PET-MRI scanner in accordance with exemplary embodiments of the present disclosure.

FIG. 1 is illustrative of a hybrid or combined Positron Emission Tomography (PET)-Magnetic Resonance Imaging (MRI) scanner 10. The scanner 10 can generally extend longitudinally along a longitudinal axis L from a proximal end 12 to the distal end 14. The scanner 10 can include MRI components 16 forming an MRI scanner portion configured to acquire MR data, PET imaging components 18 forming a PET image scanner portion configured to acquire PET image data, and a support structure, e.g., a bed 20 (or table), configured to translate along the longitudinal axis L from the proximal end 12 to the distal end 14 to position the bed 20 with respect to a field of view (FOV) of the MRI scanner portion and a FOV of the PET scanner portion.

The MRI components 16 can include a magnet assembly 22 and a gradient coil assembly 24, which can be implemented separately or as part of the magnet assembly 22. The magnet assembly 22 can include a polarizing main magnet 26. The MRI components 16 can include an RF coil assembly 28, which can be implemented as a radio frequency (RF) transmit coil and a phased array receive coil. The RF coil assembly 28 can be configured to transmit RF excitation pulses and to receive MR signals radiating from the subject in response to the RF excitation pulses. The gradient assembly 24 can include one or more physical gradient coils (e.g., three gradient coils having orthogonal axes) to produce magnetic field gradients to spatially encode acquired MR data output from the scanner 10 according to a k-space or raw data matrix. In exemplary embodiments, one or more k-space trajectories can be implemented, such as a Cartesian k-space trajectory, spiral k-space trajectory, cone k-space trajectory, radial k-space trajectory, and/or any other suitable k-space trajectory.

The PET imaging components 18 of the scanner 10 can include a positron emission detector 30, configured to detect gamma rays from positron annihilations emitted from a subject. Detector 30 can include scintillators and photovoltaic detection electronics. The detector 30 can be of any suitable construction and have any suitable arrangement for acquiring PET data. For example, in exemplary embodiments, the detector 30 can have a ring configuration. Gamma ray incidences detected by the scintillators of the detector 30 can be transformed, by the photovoltaic detection electronics of the detector 30, into electrical signals, which can be conditioned and processed to output digital signals that can match pairs of gamma ray detections as potential coincidence events. When two gamma rays strike detectors approximately opposite one another, it is possible, absent the interactions of random noise and signal gamma ray detections, that a positron annihilation took place somewhere along the line between the detectors. The coincidences can be sorted and integrated as PET data that can be processed and/or stored via a computing system 40.

In an exemplary embodiment, the scanner 10 can include a control system 50 having a processing device, e.g., controller 52, for controlling an operation of the scanner 10. The controller 52 of the control system 50 can be programmed and/or configured to control an operation of the MRI components 16, PET components 18, and/or bed 20. While the control system 50 is depicted as being included in the scanner 10, those skilled in the art will recognize that the control system 50, or portions thereof, can be implemented separately and apart from the scanner 10 and can be communicatively coupled to the scanner 10. The control system 50 can be in communication with a computing device 40 such that the scanner 10 can be programmed and/or controlled, via a computing system 40 communicatively coupled to the control system 50 to transmit data and/or commands to the controller 52 of the control system 50 to control an operation of the scanner 10. In some embodiments, the computing device 40 can be in communication with the control system 50 via a communications network 54.

In exemplary embodiments, the computing system 40 can configure and/or program the controller 52 of the control system 50 to control the MRI components 16, PET components 18, and/or the bed 20 to perform a scan sequence in response to instructions, commands, and/or requests transmitted to the control system 50 by the computing device 40. As one example, the controller 52 of the control system 50 can be programmed to acquire a sequence of PET images according to a schedule by passing the bed, upon which the subject is supported, through the field of view of the PET scanner portion of the scanner 10. As another example, the controller 52 of the control system can be programmed and/or configured (e.g., via the computing device 40) to generate RF and gradient pulses of a scan sequence for acquisition of MR images. Some of these pulses can have a timing, strength, and shape corresponding to a timing and length of a data acquisition window over which the MR data are to be acquired.

Gradient pulses can be produced during the MR data acquisition by controlling one or more physical gradient coils in a gradient coil assembly 24 to produce magnetic field gradients to spatially encode acquired MR data output from the scanner 10 in one or more lines of k-space. MR signals resulting from the excitation pulses, emitted by excited nuclei in a subject, can be sensed by the RF coil assembly 28, and can be provided to the computing system for processing. MR data can be collected and output as one or more sets of raw k-space data. The raw k-space data can be utilized in reconstruction (e.g., via Fourier transform) of MR image data by the computing device 40 and/or another device. In some embodiments, PET data and MR data can be concurrently acquired by the scanner 10.

In exemplary embodiments, the field of view (FOV) of the MR data acquisition can be shifted by the control system 50 (e.g., at the direction of the computing device 40). For example, a location of the FOV can be controlled by controlling a frequency of the MR receiver and/or a phase of the MR receiver (e.g., via the computing device 40 and/or control system 50). The FOV defines the imaging area of the MRI scanner portion such that portions of the subject that are within the FOV are imaged by the MRI scanner portion. MR data can be acquired for a subject by shifting the FOV of the MRI scanner portion and/or by adjusting a position of the bed 20 with respect to the FOV. For example, a full/whole-body MR scan of a patient can be accomplished by positioning the bed 20 within the scanner 10 and acquiring MR data for different fields of view and/or by maintaining a static field of view and passing the bed 20, upon which the subject is supported, through the field of view.

In an exemplary operation of the scanner 10, the controller 52 of the control system 50 advances the bed 20 (either continuously or in stages) into the scanner 10 along the longitudinal axis L from the proximal end 12 towards the distal end 14. As the bed 20 is advanced, a series of rapid MR scout images is acquired (e.g., coronal images with approximately 1 second for each image acquisition) from head to toe (or in the reverse order if the patient is positioned feet-first). A PET acquisition schedule can be programmatically generated (e.g., by the controller 52 and/or computing device 40) based on an anatomy identified in the MR scouts and the controller 52 of the control system 50 can control the scanner 10 according to the PET acquisition schedule.

The anatomy of the subject can be identified from the MR scout images by generating (via the computing device 40) an anatomy map that includes an outline of the subject's body and the location of major organs such as the lungs. The outline can be generated based on a pixel intensity contrast between the subject's body and the surrounding environment of the subject (e.g., air). The outline generated by the computing device 40 can be used to determine an orientation of the subject on the bed 20 for example by identifying the legs and head of the subject. Using the outline and organ locations, the schedule of PET scans can be generated (via the controller 52 and/or computing device) to segment the scans according to the anatomy and orientation of the subject as well as the height of the subject so that the scheduled scans can integrally cover the subject's anatomy.

Alternatively, the anatomy can be recognized from the MR images through a variety of established techniques. As an example, the cardiac anatomy can be automatically identified using methods similar to that described in U.S. Pat. No. 8,165,377. These classes of techniques uses direct identification of anatomical landmarks. The use of a combination of body outline/contours and also anatomical organ landmarks also represent one embodiment of the automatic anatomy identification/recognition step.

The PET acquisition schedule can include PET scan parameters including a sequence of bed positions at which PET scans are to be acquired and PET scan duration or acquisition time for each bed position in the sequence. In exemplary embodiments, scan durations can be based on expected PET attenuation for a given region of the subject and/or on whether retrospective respiratory gating will be used at a given bed position. For example, the MR scouts can be processed to identify portions of the anatomy that have less attenuation than other portions of the anatomy of the subject and the schedule can be generated to specify a shorter scan duration for the portions of the anatomy having less attenuation. In some embodiments, the attenuation coefficients can be determined based on a cross-sectional area of a slice of the MR scout images transverse to the longitudinal axis, where a portion of the anatomy that has a smaller cross-sectional area (e.g., the legs) generally corresponds to a smaller attenuation than a portion of the anatomy (e.g., the abdomen) that has a larger cross-sectional area. In other embodiments, the MR scout images can be segmented into different tissue types (e.g. muscle or bone) using segmentation techniques known in the art, and this information used to refine the attenuation coefficients. Retrospective gating can be applied to the PET data using a gating device, simultaneous MR motion data, PET device-less gating, and/or using any other suitable techniques. Using the schedule, the controller 52 can move the bed 20 to each position in the sequence and can acquire PET data at each position according to the scan duration for that position and/or whether respiratory gating will be used. In exemplary embodiments, MR data can be acquired concurrently with the PET data.

Figure 2:
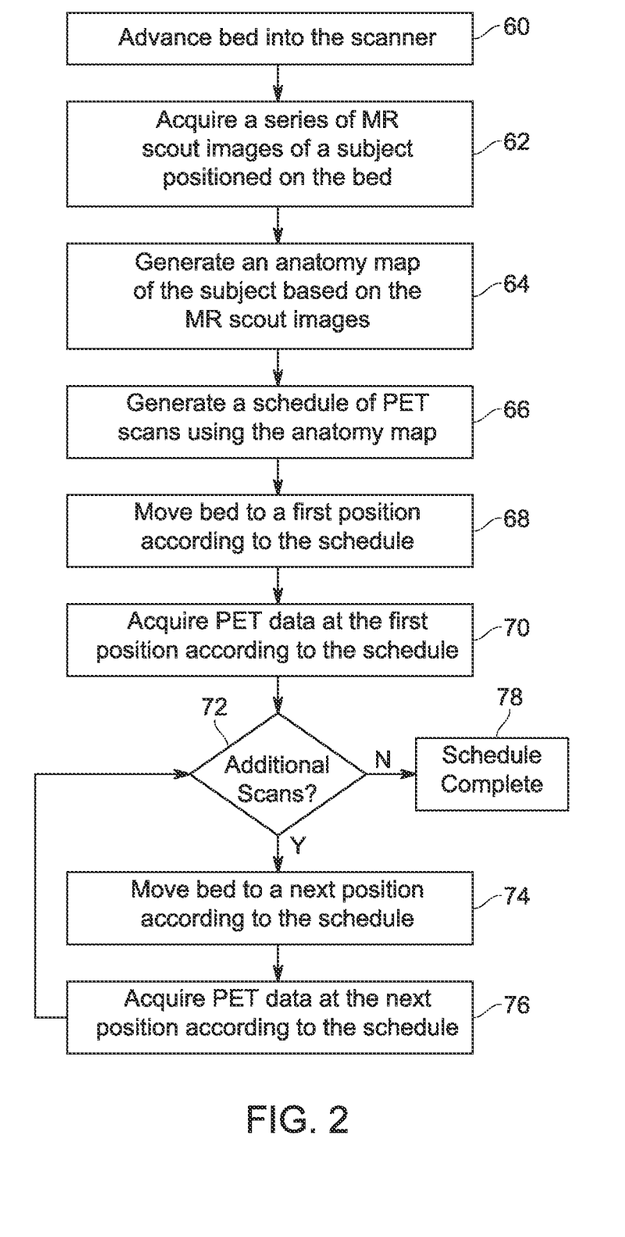
FIG. 2 is a flowchart of an exemplary scheduling and scanning process that can be implemented using an embodiment of the combined PET-MRI scanner of FIG. 1.

FIG. 2 is a flowchart of an exemplary scheduling process that can be implemented in accordance with exemplary embodiments of the present disclosure. To begin, a PET agent is administered to a subject (e.g., a human patient). The subject is supported by the bed of the scanner and the bed is advanced into the scanner (60). The bed can be advanced into the PET-MR scanner along the longitudinal axis through the proximal end of the scanner and towards the distal end of the scanner. As the bed is advanced—either continuously or in stages—a series of MR scout images (e.g., coronal or low-resolution 3D images) is acquired over the body of the subject (e.g., from head to toe or vice versa) (62). The MR scout images are "stitched" together into an anatomy map of the subject (64). The acquisition of the MR scout images can begin in response to initiation of the bed advancement into the bore of the scanner.

Using the anatomy of the subject captured in the MR scout images, a schedule of PET scans to be acquired is programmatically generated (66). The schedule can include a sequence of bed positions at which PET data are to be acquired and a scan duration for each bed position. In an exemplary embodiment, the bed positions can be specified to ensure that an integral number of be positions spans the anatomy of the subject, and that positions are well segmented into moving (e.g. from respiration) and non-moving anatomy. The orientation of the patient (e.g., feet or head first) is generally irrelevant because the orientation can be determined.

The scan durations for each bed position can be determined based on an expected PET attenuation (e.g. the legs will have less attenuation and so require shorter scan durations as compared to other portions of the subject's body), and on whether retrospective respiratory gating or other motion compensation algorithms will be used at a given position. The anatomy is automatically identified for each scan position, and respiratory gating or motion compensation algorithms can be dispensed with when imaging regions where there is no respiratory motion. This applies to imaging the legs (at or below the pelvis) and also the head and neck regions.

Once the PET bed-position schedule is calculated, the bed is moved according to the schedule to a first position in the sequence of bed positions (68), and PET imaging is commenced at the first bed position for a scan duration corresponding to the first bed position in the sequence of bed positions (70). If there are additional bed positions in the schedule (72), the bed is moved to the next bed position in the schedule (74) and PET imaging (and MR imaging) is commenced at the next bed position for the scan duration corresponding to the next bed position (76). If there are no more bed positions (72), the schedule has been complete and the bed is moved out of the scanner to allow the patient to dismount from the bed (78). In some embodiments, MR imaging can also be conducted simultaneously with PET data acquisition at some or all of the different bed positions in the sequence of bed positions.

Figure 3:
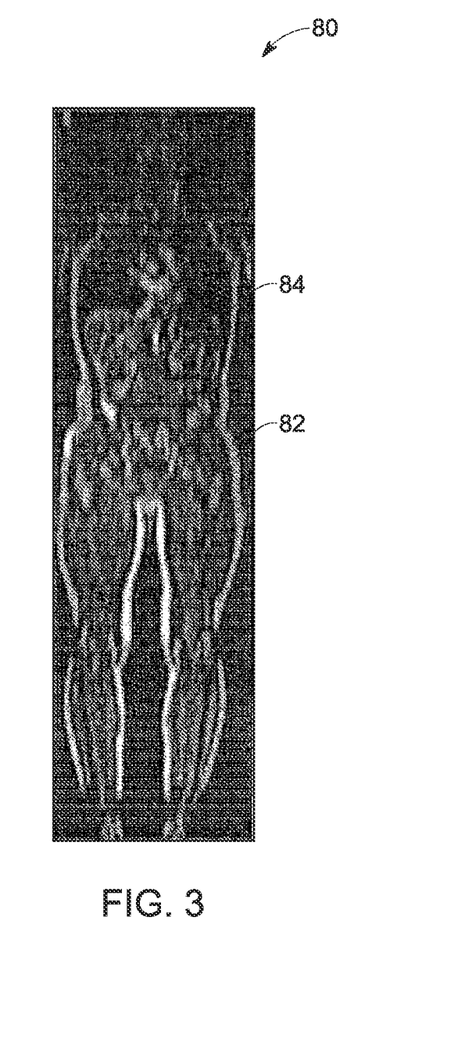
FIG. 3 is an exemplary anatomy map that can be generated using MR scout images acquired in accordance with exemplary embodiments of the present disclosure.

FIG. 3 is an exemplary anatomy map 80 of a subject that can be generated using acquired MR scout images. In exemplary embodiments, the MR scout images can be coronal scout images that are acquired as the bed of the scanner is advanced along the longitudinal axis towards the distal end of the scanner. As shown in FIG. 3, the anatomy map 80 can form an outline 82 of the subject to identify a boundary between the subject and the subject's surrounding environment. The anatomy map 80 can provide crude details of the internal structure 84 of the subject, which together with the outline 82, can be used to generate the scan schedule. The anatomy map 80 together with the outline 82 can also be used to identify the appropriate anatomy-specific detection algorithm, depending on the bed position. The ability to provide more detailed anatomy-specific identification also aids in more accurate assignment of tissue-specific attenuation coefficients for the PET image reconstruction. Anatomy-specific identification also aids in selecting the appropriate anatomy segmentation algorithms. As an example, a different anatomy segmentation approach is used for the brain as opposed to that used for the anatomical structures in the abdomen.

Figure 4:
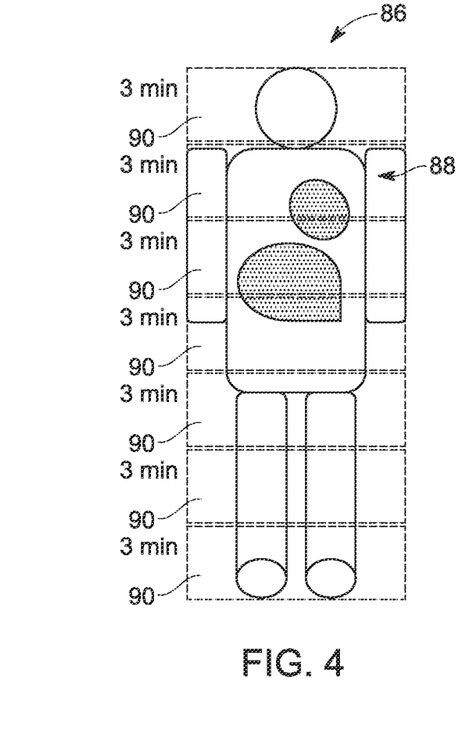
FIG. 4 illustrates a scan schedule that can be generated based on MR scout images of a subject in accordance with exemplary embodiments of the present disclosure.

FIG. 4 illustrates a basic scan schedule 86 generated using conventional scheduling techniques. As shown in FIG. 4, a whole body PET scan of a subject 88 is planned. The schedule 86 includes a sequence of scans 90 (e.g., from head to toe or vice versa) each corresponding to a position of a subject 88 on a bed with respect to the field of view of the PET scanner portion of the PET-MRI scanner. The scan durations for each position can be uniform (e.g., three minutes per scan) such that the duration of each scan is substantially identical and does not account for different attenuation coefficients associated with different portions of the subject's body and/or whether respiratory gating will be used.

Figure 5:
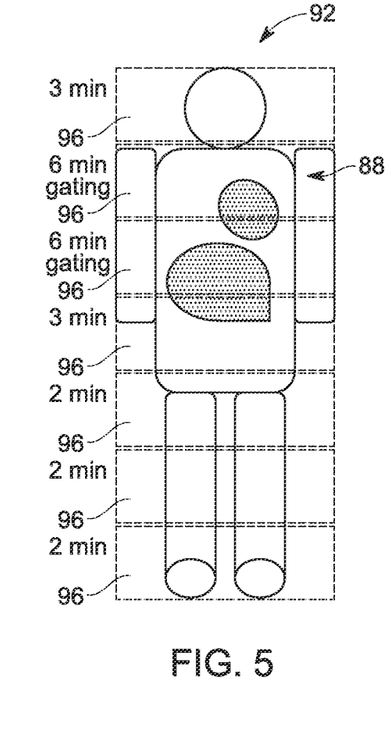
FIG. 5 illustrates another scan schedule that can be generated based on MR scout images of a subject in accordance with exemplary embodiments of the present disclosure.

FIG. 5 illustrates another scan schedule 92 that can be generated based on MR scout images of the subject 88 in accordance with exemplary embodiments of the present disclosure. As shown in FIG. 5, a whole body PET scan of a subject 88 is planned based on an anatomy map of the subject 88 generated using MR scout images acquired for the subject 88. The schedule 92 includes a sequence of scans 96 (e.g., from head to toe or vice versa) each corresponding to a position of a subject 88 on a bed with respect to the field of view of the PET scanner portion of the PET-MRI scanner. The scan durations for each position can be specified based on the anatomy map to improve the efficiency of the PET-MRI scanner, by modifying the scan duration, as compared to the schedule 86 of FIG. 4. The bed positions can be arranged to insure that an integral number of positions spans the anatomy, and that the bed positions are specified to provide well segmented scanning separating moving (e.g. from respiration) and non-moving anatomy into different scans. The scan durations at each position are assigned based on expected PET attenuation (e.g. the legs will have less attenuation and so require shorter scan durations), and on whether retrospective respiratory gating will be required at a given position. Because the anatomy is automatically identified for each scan position, respiratory gating can be dispensed with when imaging regions where there is no respiratory motion. This applies to imaging the legs (at or below the pelvis) and also the head and neck regions. Additionally, respiratory gating can be automatically specified based on the identified anatomy so that, for example, a scheduled scan of the lungs can use one or more respiratory gating techniques.

Figure 6:
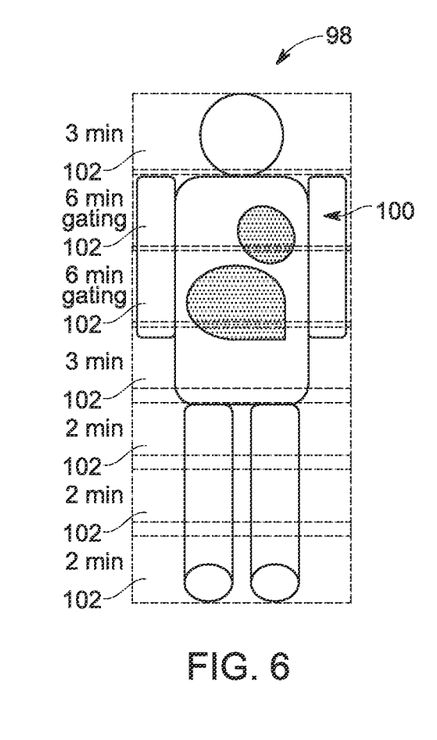
FIG. 6 illustrates yet another scan schedule that can be generated based on MR scout images of a subject in accordance with exemplary embodiments of the present disclosure.

FIG. 6 illustrates a scan schedule 98 that can be generated based on MR scout images of a subject 100 in accordance with exemplary embodiments of the present disclosure. The subject 100 can be smaller than the subject 88 shown in FIGS. 4 and 5. As shown in FIG. 6, a whole body PET scan of a subject 100 is planned based on an anatomy map of the subject 100 programmatically generated using MR scout images acquired for the subject 100. The schedule 98 includes a sequence of scans 102 (e.g., from head to toe or vice versa) each corresponding to a position of a subject 100 on a bed with respect to the field of view of the PET scanner portion of the PET-MRI scanner. As shown in FIG. 6, the scheduled scans have a greater overlap that than the scheduled scans shown in FIG. 5. The scan durations for each position can be specified based on the anatomy map to improve the efficiency of the PET-MRI scanner.

Figure 7:
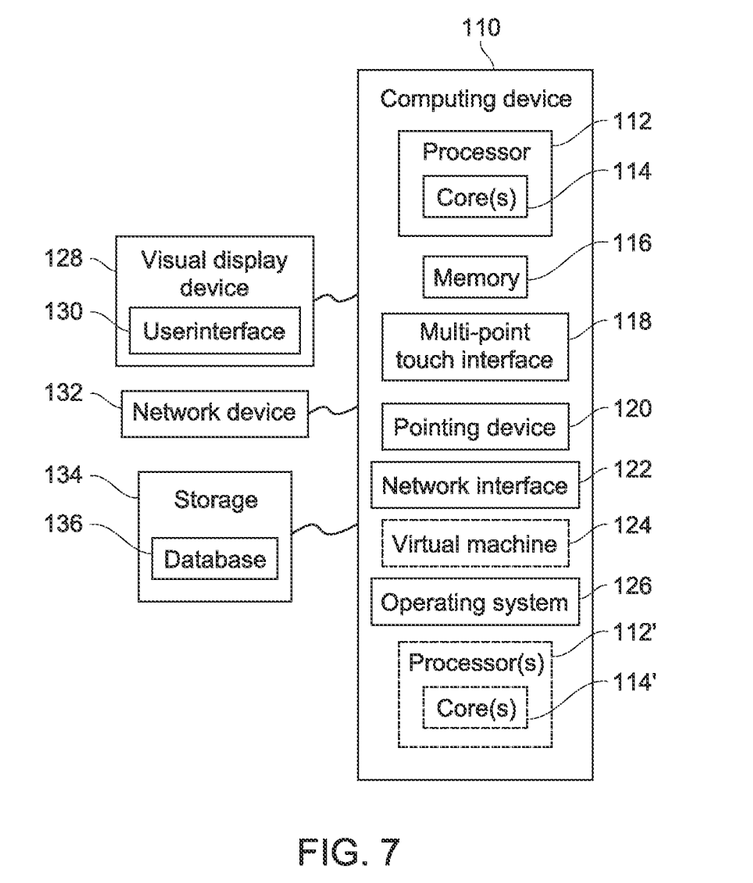
FIG. 7 is an exemplary computing device for implementing exemplary embodiments of the present disclosure.

FIG. 7 is a block diagram of an exemplary computing device 110 that may be used to implement exemplary embodiments of the present disclosure. For example, the computing device 110 can correspond to the computing device 40 of FIG. 1. The computing device 110 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 116 included in the computing device 110 may store computer-readable and computer-executable instructions or software for interface with and/or controlling an operation of the scanner 10. The computing device 110 also includes configurable and/or programmable processor 112 and associated core 114, and optionally, one or more additional configurable and/or programmable processing devices, e.g., processor(s) 112' and associated core(s) 114' (for example, in the case of computer systems having multiple processors/cores), for executing computer-readable and computer-executable instructions or software stored in the memory 116 and other programs for controlling system hardware. Processor 112 and processor(s) 112' may each be a single core processor or multiple core (114 and 114') processor.

Virtualization may be employed in the computing device 110 so that infrastructure and resources in the computing device may be shared dynamically. A virtual machine 124 may be provided to handle a process running on multiple processors so that the process appears to be using only one computing resource rather than multiple computing resources. Multiple virtual machines may also be used with one processor.

Memory 116 may include a computer system memory or random access memory, such as DRAM, SRAM, EDO RAM, and the like. Memory 116 may include other types of memory as well, or combinations thereof.

A user may interact with the computing device 110 through a visual display device 128, such as a computer monitor, which may display one or more user interfaces 130 that may be provided in accordance with exemplary embodiments. The computing device 110 may include other I/O devices for receiving input from a user, for example, a keyboard or any suitable multi-point touch interface 118, a pointing device 120 (e.g., a mouse). The keyboard 118 and the pointing device 120 may be coupled to the visual display device 128. The computing device 110 may include other suitable conventional I/O peripherals.

The computing device 110 may also include one or more storage devices 134, such as a hard-drive, CD-ROM, or other computer readable media, for storing data and computer-readable instructions and/or software that interface with and/or control an operation of the scanner 10 described herein. Exemplary storage device 134 may also store one or more databases for storing any suitable information required to implement exemplary embodiments. For example, exemplary storage device 134 can store one or more databases 136 for storing information, such as scan sequences, scan schedules, anatomy maps, MR scout data, MR data, PET data, MR scout images, MR images, PET images, PET attenuation coefficients, and/or any other information that can be used to implement exemplary embodiments of the present disclosure. The databases may be updated by manually or automatically at any suitable time adding, deleting, and/or updating one or more items in the databases.

The computing device 110 can include a network interface 122 configured to interface via one or more network devices 132 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 122 may include a built-in network adapter, network interface card, PCMCIA network card, card bus network adapter, wireless network adapter, USB network adapter, modem or any other device suitable for interfacing the computing device 110 to any type of network capable of communication and performing the operations described herein. Moreover, the computing device 110 may be any computer system, such as a workstation, desktop computer, server, laptop, handheld computer, tablet computer, or other form of computing or telecommunications device that is capable of communication and that has sufficient processor power and memory capacity to perform the operations described herein.

The computing device 110 may run any operating system 126, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 126 may be run in native mode or emulated mode. In an exemplary embodiment, the operating system 126 may be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

The exemplary flowchart in FIG. 2 is herein for illustrative purposes and shows non-limiting examples of methods. One of ordinary skill in the art will recognize that exemplary methods may include more or fewer steps than those illustrated in the exemplary FIG. 2, and that the steps in the exemplary flowcharts may be performed in a different order than the order shown in the illustrative flowcharts.

The invention claimed is:
1. A method of operating a combined PET-MRI scanner comprising:

acquiring a sequence of MR scout images of a subject with a processing device in communication with MR imaging components to acquire the sequence of the MR scout images of the subject via a MRI scanner portion of the combined PET-MRI scanner;

automatically determining an anatomy and an orientation of the subject at various table positions with the processing device based on the MR scout images; and automatically generating a sequence of table positions and scan durations for each table position for acquiring PET scans of the subject with the processing device in communication with PET imaging components and the MR imaging components to acquire a sequence of PET scans of the subject via a PET scanner portion and according to the sequence programmatically generated based on the anatomy of the subject determined from the MR scout images, wherein each of the scan durations are determined based on at least one of an expected PET attenuation or whether retrospective respiratory gating will be used for a region identified in the MR scout images.

2. The method of claim 1, wherein the table is automatically moved along a longitudinal axis with respect to an MRI scanner portion of the combined PET-MRI scanner, and wherein the table is automatically moved through a field of view of the MRI scanner portion to acquire the sequence of MR scout images along at least a portion of a length of the table.

3. The method of claim 2, further comprising acquiring at least one of the PET scans of the sequence of PET scans at each of the table positions.

4. The method of claim 3, wherein the sequence includes an acquisition time associated with each of the table positions and the method further comprises acquiring the at least one of the PET scans at each of the table positions according to the acquisition time.

5. The method of claim 4, further comprising calculating the acquisition time based on the anatomy of the subject determined from the MR scout images.

6. The method of claim 4, further comprising identifying the PET scans of the sequence of PET scans for which respiratory gating or motion compensation algorithm will be used.

7. The method of claim 4, further comprising calculating the table positions to separate moving anatomy PET scans from non-moving anatomy scans based on the MR scout images.

8. The method of claim 1, wherein the anatomy determined from the MR scout images are represented in an anatomy map and an orientation of the subject is determined based on the anatomy map.

9. The method of claim 1, wherein the table is automatically moved along a longitudinal axis with respect to an MRI scanner portion of the combined PET-MRI scanner to acquire the MR scout images; and wherein the table is automatically moved along the longitudinal axis with respect to the PET scanner portion of the combined PET-MRI scanner to acquire at least one of the PET scans of the sequence of PET scans at a sequence of table positions according to the sequence.

10. A non-transitory computer-readable storage medium storing executable instruction, wherein execution of the instructions by a processing device causes the processing device to implement a method comprising:

acquiring a sequence of MR scout images of a subject with the processing device in communication with MR imaging components to acquire the sequence of the MR scout images of the subject via a MRI scanner portion of the combined PET-MRI scanner;

automatically determining an anatomy and an orientation of the subject at various table positions with the processing device based on the MR scout images; and automatically generating a sequence of table positions and scan durations for each table position for acquiring PET scans of the subject with the processing device in communication with PET imaging components and the MR imaging components to acquire a sequence of PET scans of the subject via a PET scanner portion and according to the sequence programmatically generated based on the anatomy of the subject determined from the MR scout images, wherein each of the scan durations are determined based on at least one of an expected PET attenuation or whether retrospective respiratory gating will be used for a region identified in the MR scout images.

11. The medium of claim 10, wherein an acquisition time is specified based on the anatomy of the subject determined from the MR scout images, and wherein a table is automatically moved along a longitudinal axis with respect to an MRI scanner portion of the combined PET-MRI scanner to acquire the MR scout images; and wherein the table is automatically moved along the longitudinal axis with respect to the PET scanner portion of the combined PET-MRI scanner to acquire at least one of the PET scans of the sequence of PET scans at each of the table positions according to the sequence.

12. The medium of claim 10, wherein the method implemented by the execution of the instructions further comprises:

calculating the table positions to separate moving anatomy PET scans from non-moving anatomy scans based on the MR scout images; and identifying the PET scans of the sequence of PET scans for which respiratory gating will be used.

* * * * *